United States Patent
Blum

(10) Patent No.: US 10,894,024 B2
(45) Date of Patent: Jan. 19, 2021

(54) ANTI-RDS COMPOUNDS AND METHOD OF MANUFACTURE AND ADMINISTRATION THEREOF TO INDUCE DOPAMINE HOMEOSTATIS

(71) Applicant: SYNAPTAMINE, INC., Austin, TX (US)

(72) Inventor: Kenneth Blum, Austin, TX (US)

(73) Assignee: SYNAPTAMINE, INC., Austin, TX (US)

(*) Notice: Subject to any disclaimer, the term of this patent is extended or adjusted under 35 U.S.C. 154(b) by 0 days.

(21) Appl. No.: 15/534,372

(22) PCT Filed: Dec. 7, 2015

(86) PCT No.: PCT/US2015/064309
§ 371 (c)(1),
(2) Date: Jun. 8, 2017

(87) PCT Pub. No.: WO2016/094316
PCT Pub. Date: Jun. 16, 2016

(65) Prior Publication Data
US 2017/0360734 A1    Dec. 21, 2017

Related U.S. Application Data

(60) Provisional application No. 62/089,177, filed on Dec. 8, 2014.

(51) Int. Cl.
*A61K 31/198* (2006.01)
*A61K 9/107* (2006.01)
*A61K 9/20* (2006.01)
*A61K 9/127* (2006.01)
*A61K 9/08* (2006.01)
*A61K 38/05* (2006.01)

(52) U.S. Cl.
CPC ............. *A61K 31/198* (2013.01); *A61K 9/08* (2013.01); *A61K 9/1075* (2013.01); *A61K 9/127* (2013.01); *A61K 9/2077* (2013.01); *A61K 38/05* (2013.01)

(58) Field of Classification Search
None
See application file for complete search history.

(56) References Cited

U.S. PATENT DOCUMENTS

2009/0280195 A1* 11/2009 Hoshour ................ A61K 36/48
424/725
2011/0189161 A1* 8/2011 Blum ..................... A61K 45/06
424/94.65

\* cited by examiner

*Primary Examiner* — Dennis J Parad

(57) ABSTRACT

Compounds for treating reward deficiency syndrome (RDS) behaviors and methods of use and administration of such compounds to induce dopamine homeostasis. These compounds synergistically combine two or more of (a) DPA, (b) NAC, and (c) kyotorphin (or arginine and tyrosine, the precursors of kyotorphin). These work together to enhance dopamine release by employing mechanisms tied to GABA regulation on Dorsal Raphe VGlut3 neurons via the Substania Nigra and increasing enkephalins (by increasing the release of enkepahlins and by the inhibition of enkephalinase). The resulting compound can induce dopamine homeostatis (and thus induce anti-stress states and diminish stress induced addictive behaviors). In embodiments of the present invention, the compound further includes nano-sized particles that enable the compound to be water- or powder-based even though DPA, NAC, and kyotorphin are not soluble in water.

12 Claims, 7 Drawing Sheets

ANTI-RDS COMPOUNDS AND METHOD OF MANUFACTURE AND ADMINISTRATION THEREOF TO INDUCE DOPAMINE HOMEOSTATIS

RELATED PATENT APPLICATIONS

This application is a § 371 National Phase Application of PCT International Patent Appl. No. PCT/US2015/064309, filed on Dec. 7, 2015, entitled "Anti-RDS Compounds And Method Of Manufacture And Administration Thereof To Induce Dopamine Homeostatis" which claims the benefit of provisional U.S. Patent Application Ser. No. 62/089,177, filed on Dec. 8, 2014, entitled "Coupling Anti-Reward Deficiency Syndrome Compounds and Aqua-Nano-Technology." These patent applications are commonly assigned to the Assignee of the present invention and is hereby incorporated herein by reference in their entirety for all purposes.

TECHNICAL FIELD

This disclosure relates to compounds for treating reward deficiency syndrome (RDS) behaviors and methods of use and administration of such compounds to induce dopamine homeostasis.

BACKGROUND

In 2013, it was noted in Blum 2013, Chapter 2, Section, 2.5, p. 39: When almost half-of the US population have indulged in illegal drug practices, when our presidential candidates are forced to dodge the tricky question of their past history involving illegal drug use, and when almost every American has sloshed down a martini or two in their life time, there must be a reason, there must be a need, there must be a natural response for humans to imbibe at such high rates. There is even a more compelling question surrounds the millions who seek out high risk novelty. Why do millions have this innate drive in face of putting themselves in Harm's way? Why are millions paying the price of their indiscretions in our jails, in hospitals, in wheel chairs and are lying dead in our cemeteries. What price must we pay for pleasure seeking or just plain getting "HIGH"? Maybe the answer lies within our brain. Maybe it is in our genome?

Reward Deficiency Syndrome (RDS) was first defined by the inventor and his lab in 1996 as a putative predictor of impulsive and addictive behaviors. [Blum 2000; Blum 1996; Comings 2000]. RDS is now to be featured in SAGE Encyclopedia of Abnormal Psychology (2016). See also TABLE 1.

TABLE 1

The Reward Deficiency Syndrome Behaviors (RDS).

| ADDITIVE BEHAVIORS | | | | | |
|---|---|---|---|---|---|
| | Non | IMPULSE BEHAVIORS | | OBESSIVE | |
| Substance Related | Substance Related | Spectrum Disorders | Disruptive Impulsive | COMPULSIVE BEHAVIORS | PERSONALITY DISORDERS |
| Alcohol | Thrill seeking (novelty) | Attention-deficit Hyper-activity | Anti-social | Body Dys-morphic | Paranoid |
| Cannabis | Sexual Sadism | Tourette and Tic Syndrome | Conduct | Hoarding | Schizoid |
| Opioids | Sexual Masochism | Autism | Intermittent Explosive | Trichotillo-mania (hair pulling) | Borderline |
| Sedatives/Hypnotics | Hypersexual | | Oppositional Defiant | Excoriation (skin picking) | Schizotypal |
| Stimulants | Gambling | | Exhibitionistic | Non-suicidal Self-Injury | Histrionic |
| Tobacco | Internet Gambling | | | | Narcissistic |
| Glucose | | | | | Avoidant |
| Food | | | | | Dependent |

The molecule dopamine (DA) after binding to the dopamine D2 receptor has been associated with many behaviors [Dackis 1985; Di Chiara 1988] and the DRD2 has been referred to as a reward gene [Blum I 1990; Eisenberg 2007; Hietala I 1994; Hietala II 1994; Volkow 2001; Volkow 2002]. Although the DRD2 gene and especially the TaqI A1 allele have been most associated with neuropsychiatric disorders in general, in alcoholism, and other addiction (carbohydrate) reward behaviors, it may also be involved in co-morbid antisocial personality disorder symptoms (especially in children and adults with attention deficit hyperactivity disorder (ADHD) or Tourette's Syndrome) and high novelty seeking.

The brain reward circuitry, in particular, the dopaminergic system and the dopamine D2 receptor, has been implicated in reward mechanisms. [Blum I 1990]. The net effect of neurotransmitter interaction at the mesolimbic brain region induces "reward" when dopamine (DA) is released from the neuron at the nucleus accumbens and interacts with a dopamine D2 and D1 receptors. [Blum 1996; Blum 2000; Volkow et al. 2001].

Dopamine has been called the "anti-stress molecule" and/or the "pleasure molecule." [Blum I 1990; Hall 1977; Blum 1996]. When dopamine is released into the synapse, it stimulates a number of receptors (D1-D5), which results in increased feelings of well-being and stress reduction [Picetti 2013; Blum 2000].

The mesocorticolimbic dopaminergic pathway plays an especially important role in mediating the reinforcement of natural rewards like food and sex, as well as unnatural rewards like drugs of abuse [Melis 2005]. Natural rewards include satisfaction of physiological drives (e.g., hunger and reproduction) and unnatural rewards are learned and involve satisfaction of acquired pleasures such as hedonic sensations derived from alcohol and other drugs, as well as from gambling and other risk-taking behaviors. [Blum 1996; Blum 2013; Blum 2014]. Utilizing positron emission tomography (PET) others have found substantial lower levels of D2 receptors in alcohol and drug dependent subjects compared to non-dependent individuals. [Volkow 1996]. In animals, over expression of the D2 receptor via vector delivery of the D2 gene directly into the nucleus accumbens resulted in significant reduction of alcohol consumption [Myers 1999; Thanos 2001].

Dopamine must be regulated to reduce aberrant craving and drug seeking and all addictive behaviors including process addiction (RDS). In terms of therapeutic targets it is believed that each genetic cluster is regulated by a master gene programmer and will need to be identified across the central nervous system (CNS) as an example, especially along the brain reward circuitry. The damage to DNA along this reward circuitry results in diminished dopaminergic activity. This sets up the brain to be more sensitive to stress especially in the aged individual. There are many genes involved in this system but it is known that the normal function of this important reward system works as a cascade known as the "brain reward cascade."

FIG. 1A illustrates the brain reward cascade 100. [Blum II 1990]. The brain reward cascade 100 (also referred to as the "reward cascade") involves the release of serotonin 101, which in turn at the hypothalamus 102 stimulates enkephalin 103. The enkephalin 103 in turn inhibits GABA 104 at the substantia nigra 105, which in turn regulates the amount of dopamine 106 released at the nucleus accumbens 108 (or "reward site"). The dopamine 106 is originated at the ventral tegmental area 107.[Gessa 1985; Yadid 1994; Parsons 1996]. Various receptors (including 5HT2a receptors 109, μ-opiate receptors 110, $GABA_A$ receptors 111, $GABA_B$ receptors 112, and dopamine receptors 113) are utilized in reward cascade 100. It is well known that under normal conditions dopamine 106 in the nucleus accumbens 108 works to maintain a person's normal drives. [Adler 2000; Kelley 2002, Robbins 1996].

For more than 40 years it has been recognized that the Dorsal Raphe Nucleus (DRN-classified as a serotonergic structure) and the Ventral Tegmental Area (VTA classified as a dopaminergic structure) are two of the more relevant brain reward areas where electrical stimulation produces responding at the highest rates and lowest thresholds (meaning very sensitive). Although multiple studies have examined both the DRN and VTA and its contribution to reward, these studies have been focused on only serotonergic effects on reward. As a result these investigations have produced conflicting results, and the true role of DRN to VTA circuitry in regulating motivated behaviors is still unknown.

Contrary to the widespread idea that the major input from DRN to VTA is serotonergic, the Morales Group in Qi 2014 found that DRN neurons expressing the vesicular glutamate transporter-3(GluT3) are the major input from DRN to VTA. Within the VTA, these DR-GlutT3 neurons mostly develop synapses on dopamine neurons; some of these dopamine neurons. Qi 2014 found, specifically innervate the n. accumbens (NAc). By genetic approaches to specifically express rhodopsin in channel DR-GlutT3 neurons, it was also found that intra-VTA light stimulation of the VGLUT3-fibers elicits AMPA-mediated excitatory currents on dopamine-neurons that innervate the NAc. Such stimulation causes dopamine release in the NAc, reinforces instrumental behaviors, and established conditioned place preference. Qi 2014's discovery, of a rewarding excitatory synaptic input to the meso-accumbens dopamine neurons by a glutamatergic projection arising selectively from neurons of the DRN that contain VGLUT3 suggested that new targets may be important to boost motivation in the RDS patient. Moreover, unpublished work from NIDA (Morales Group) also found that GABA from the Substania Nigra induces regulation of the VGLUT3 neurons and as such fine tunes the release of dopamine from the VTA to NAc.

FIG. 1B illustrates the brain reward cascade further indicating mechanisms tied to GABA regulation on Dorsal Raphe VGlut3 neurons via the Substania Nigra.

In discussing RDS, insensitivity and inefficiency in the reward system is specifically referred to. There may be a common neurocircuitry, neuroanatomy and neurobiology for multiple addictions and for a number of psychiatric disorders. [Bowirrat 2005]. Due to specific genetic antecedents and environmental influences (epigenetic) a deficiency of the D2 receptors may predispose individuals to a high risk for multiple addictive, impulsive, and compulsive behaviors. It is well known that alcohol and other drugs of abuse, as well as most positive reinforces (i.e., sex, food, gambling, aggressive thrills) cause activation and neuronal release of brain dopamine and involvement of the $Na^+/K^+$-ATPase. Dopamine release can decrease negative feelings and satisfy abnormal cravings for alcohol, cocaine, heroin and nicotine which among others are linked to low dopamine function. [Rothman 2007].

Blum '724 Patent discloses a composition for the treatment of RDS. This composition includes an opiate destruction-inhibiting amount of at least one substance which inhibits the enzymatic destruction of a neuropeptidyl opiate (endogenous opiate pepetides like enkephalin), said substance being selected from the group consisting of amino acids, peptides, and analogues or derivatives of amino acids or peptides. The composition further includes a neurotransmitter synthesis-promoting amount of at least one neurotransmitter precursor selected from the group consisting of the dopamine precursors L-Tyr, L-Phe and L-dopa, the serotonin precursors L-Trp and 5-hydroxytryptophan, and the gamma amino butyric acid (GABA) precursors L-glutamine, L-glutamic acid, and L-glutamate. The composition further includes a trytophan concentration enhancing amount of a mineral compound selected from the group consisting of chromium picolinate and chromium nicotinate. And, the composition further includes an amount of at least one substance selected from the group consisting of a *Rhodiola* extract and huperzine the amounts of said substances, said neurotransmitter precursor, said mineral compound and said *Rhodiola* extract or huperzine being chosen so that the composition is effective in reducing Attention Deficits disorder with or without hyperactivity.

A feeling of well-being can be achieved only when dopamine is released in the nucleus accumbens at balanced "dopamine homeostatic" levels. Any deviation causes "dopamine resistance" and as such could result in aberrant cravings.

Accordingly, there is a need for a compound that can target and achieve dopamine regulation, i.e., dopamine homeostasis.

There is further a need for a compound that can be administered to normalize brain impairments by activating the release of brain dopamine at the reward site and thus reduce excessive craving behaviors.

There is also a need for a compound that is able to be administered in a form that is readily and easily administered, particularly in addicts who generally have an impaired system for digesting and absorbing nutrients.

SUMMARY OF THE INVENTION

Embodiments of the present invention are compounds that synergistically combine two or more of (a) D-Phenylalanine (DPA) (such as DL-Phenylalanine (DLPA), which is a mixture of DPA and L-Phenylalanine), (b) N-acetyl-L-cysteine (NAC), and (c) kyotorphin (or arginine and tyrosine, the precursors of kyotorphin). These work together to enhance dopamine release by employing mechanisms tied to GABA regulation on Dorsal Raphe VGlut3 neurons via the Substania Nigra increasing enkephalins (by increasing the release of enkepahlins and the inhibition of enkephalinase). The resulting compound can induce dopamine homeostatis (and thus induce anti-stress states and diminish stress induced addictive behaviors). In embodiments of the present invention, the compound further includes nano-sized particles that enable the compound to be water- or powder-based even though DPA, NAC, and kyotorphin are hydrophobic.

In general, in one aspect, the invention features a composition that includes water and a plurality of nanoparticles dispersed within the water. The plurality of nanoparticles are operable to form micelles or liposomes within the water. The composition further includes at least two substances dispersed within the water. The at least two substances are at least two of (i) DPA, (ii) NAC, and (iii) a kyotorphin compound. The kyotorphin compound is (A) kyotorphin or (B) a combination of arginine and tyrosine. The plurality of nanoparticles form micelles or liposomes within the water. The at least two substances are dissolved within the micelles or liposomes.

In general, in another aspect, the invention features a method that includes dispersing a plurality of nanoparticles within water. The plurality of nanoparticles are at a concentration operable to form micelles or liposomes within the water. The method further includes dispersing at least two substances dispersed within the water. The at least two substances are at least two of (i) DPA, (ii) NAC, and (iii) a kyotorphin compound. The kyotorphin compound is (A) kyotorphin or (B) a combination of arginine and tyrosine. The at least two substances are dissolved within the micelles or liposomes.

Implementations of the inventions can include one or more of the following features:

The at least two substances can include the DPA, the NAC, and the kyotorphin compound.

The at least two substances can include the kyotorphin compound.

The kyotorphin compound can include D-kyotorphin.

The kyotorphin compound can include L-arginine and L-tyrosine.

The kyotorphin compound can include DL-arginine and DL-tyrosine.

The at least two substances can include the DPA.

The DPA can be DLPA.

The at least two substances can include the NAC.

The at least two substances can be present in the composition at a dosage operable to induce dopamine homeostasis.

The dosage can include at least two of (i) the DPA in a DPA amount in the range of 1 to 5,000 mg, (ii) the NAC in an NAC amount in the range of 1 to 10,000 mg, and (iii) the kyotorphin compound is (A) kyotorphin in a kyotorphin amount in the range of 0.1 to 5,000 mg or (B) the combination of the arginine and the tyrosine with the arginine being an arginine amount in the range of 0.1 to 1,000 grams and the tyrosine being a tyrosine amount in the range of 0.1 to 5,000 grams.

The DPA can be DLPA. The kyotorphin can include D-kyotorphin, The arginine can include L-arginine. The tyrosine can include L-tyrosine.

The DPA amount can be 1,000 mg. The NAC amount can be 2,400 mg. The kyotorphin amount can be 500 mg. The arginine amount can be 250 mg. The tyrosine amount can be 150 mg.

The DPA can be DLPA. The arginine can include DL-arginine. The tyrosine can include DL-tyrosine.

The plurality of nanoparticles can form micelles within the water with the at least two substances dissolved within the micelles.

The composition can further include an additional substance dispersed in the water. The additional substance is pyridoxal-5-phoshate (the active form of vitamin $B_6$), L-glutamine, *Rhodiola rosea* root SE, rosavin, Griffonia seed extract 5-HTP, L chromium GTF plus, passion flower SE isovitexin, glucosamine n-acetyl, arabinogalactan fiberaid AG99, aloe vera FD powder 200x, white birch bark extract, *Boswellia serrata* gum extract, *Spirulina* algae, or a combination thereof.

In general, in another aspect, the invention features a composition that includes a first nanoparticle substance that is (i) nanoparticle kyotorphin or (ii) a combination of nanoparticle arginine and nanoparticle tyrosine. The composition further includes a second nanoparticle substance including at least one of (i) nanoparticle DPA and (ii) nanoparticle NAC. The composition is operable to induce dopamine homeostasis.

In general, in another aspect, the invention features a method that includes selecting a first substance of (i) nanoparticle kyotorphin or (ii) a combination of arginine and tyrosine. The method further includes selecting a second substance comprising at least one of (i) nanoparticle DPA and (ii) nanoparticle NAC. The method further includes mixing the first substance and the second substance. The method further includes reducing the size of the first substance into nanoparticles of the first substance before, during, or after the step of mixing. The method further includes reducing size of the second substance into nanoparticles of the first substance before, during, or after the step of mixing. The steps of mixing and reducing size of the first substance and the second substance form a composition. The composition is operable to induce dopamine homeostasis.

Implementations of the inventions can include one or more of the following features:

The kyotorphin can include D-kyotorphin. The combination of arginine and tyrosine can include a combination of L-arginine and L-tyrosine. The DPA can be DLPA.

The combination of arginine and tyrosine can include a combination of DL-arginine and DL-tyrosine. The DPA can be DLPA.

The composition can be in tablet form.

The composition can be in liquid form.

The first nanoparticle substance can be (i) nanoparticle kyotorphin in a kyotorphin amount in the range of 0.1 to 5,000 mg or (ii) a combination of nanoparticle arginine and nanoparticle tyrosine, with the arginine is in an arginine amount in the range of 0.1 to 1,000 grams and the tyrosine is in a tyrosine amount in the range of 0.1 to 5,000 grams. The second nanoparticle substance can be at least one of (i) the nanoparticle DPA in a DPA amount in the range of 1 to 5,000 mg, and (ii) the nanoparticle NAC in an NAC amount in the range of 1 to 10,000 mg.

The kyotorphin can include D-kyotorphin. The combination of arginine and tyrosine can include a combination of L-arginine and L-tyrosine. The DPA can be DLPA.

The DPA amount can be 1,000 mg. The NAC amount can be 2,400 mg. The kyotorphin amount can be 500 mg. The arginine amount can be 250 mg. The tyrosine amount can be 150 mg.

The combination of arginine and tyrosine can include a combination of DL-arginine and comprises DL-tyrosine. The DPA can be DLPA.

The composition can further include an additional nanoparticle substance. The additional nanoparticle substance is pyridoxal-5-phosphate (the active form of vitamin $B_6$), L-glutamine, Rhodiola rosea root SE, rosavin, Griffonia seed extract 5-HTP, L chromium GTF plus, passion flower SE isovitexin, glucosamine n-acetyl, arabinogalactan fiberaid AG99, aloe vera FD powder 200×, white birch bark extract, Boswellia serrata gum extract, Spirulina algae, or a combination thereof.

The first nanoparticle substance can be nanoparticles having sizes in the range of 3 to 20 nm. The second nanoparticle substance can be nanoparticles having sizes in the range of 3 to 20 nm.

The first nanoparticle substance can be spherical nanoparticles. The second nanoparticle substance can be spherical nanoparticles.

In the method, the step of reducing the size of the first substance and the step of reducing the size of the second substance occur after the step of mixing.

DETAILED DESCRIPTION

Figure 1A:
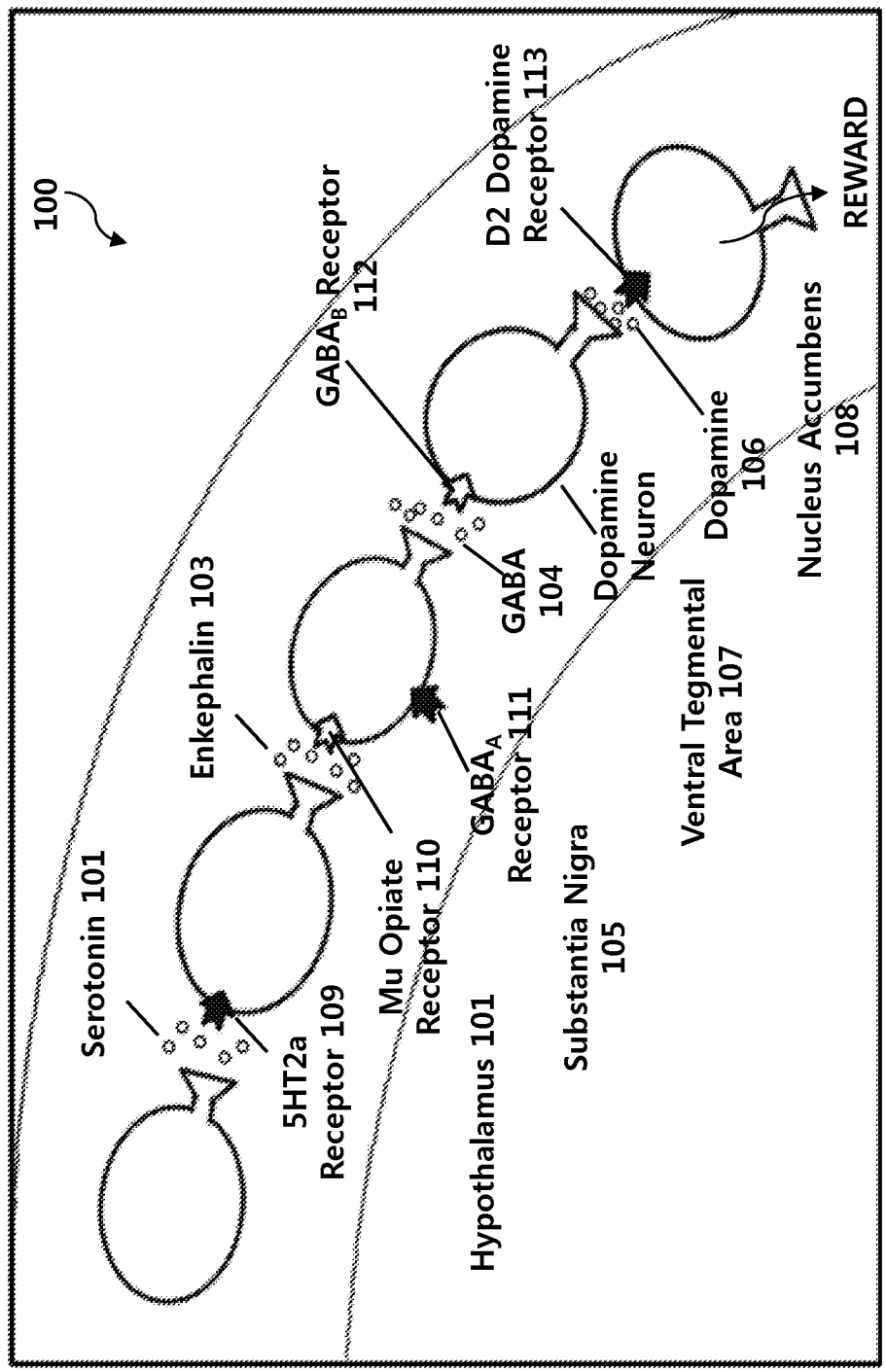
FIG. 1A illustrates the brain reward cascade.
Figure 1B:
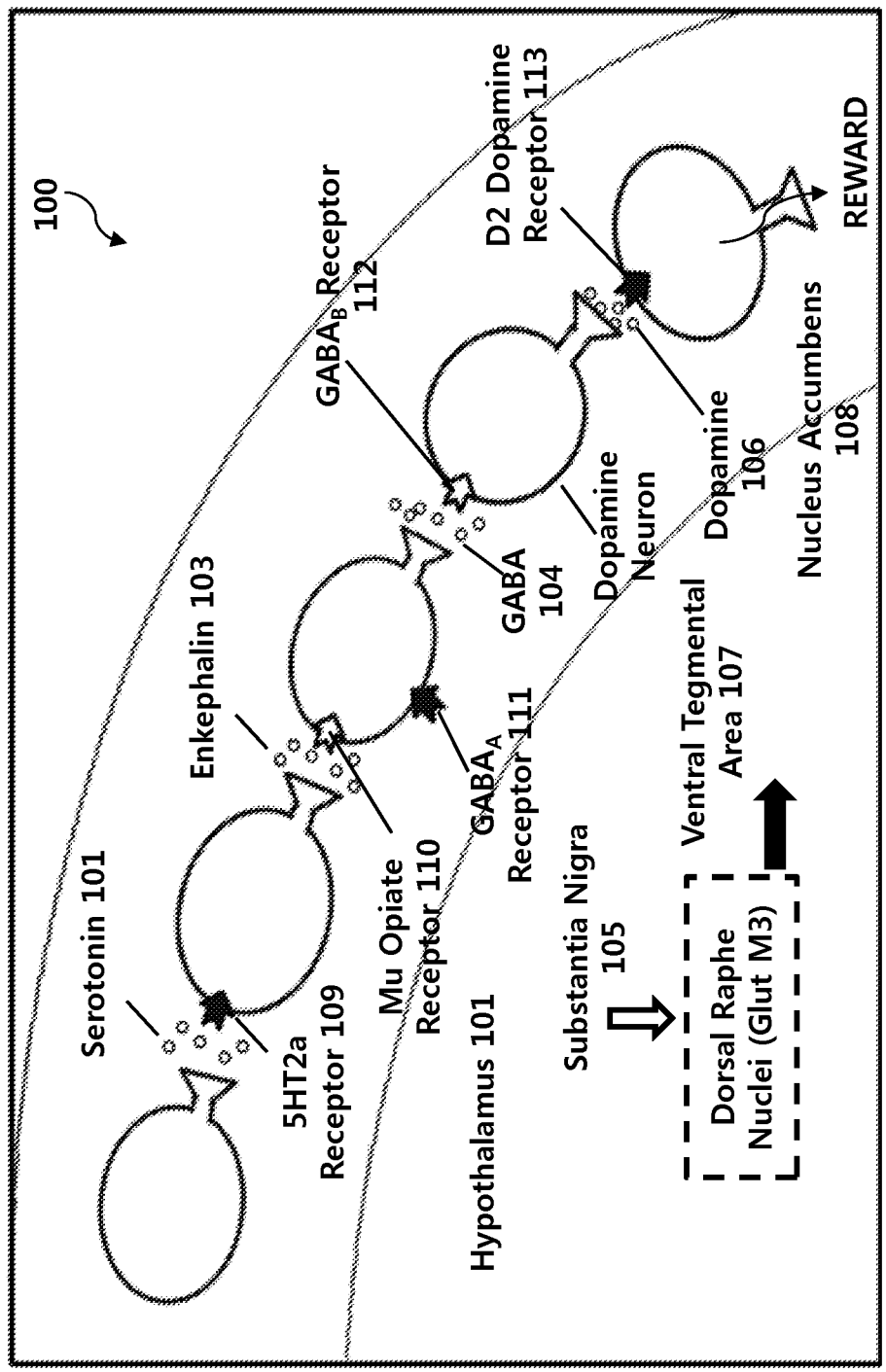
FIG. 1B illustrates the brain reward cascade further indicating mechanisms tied to GABA regulation on Dorsal Raphe VGlut3 neurons via the Substania Nigra.

Embodiments of the present invention are compounds that synergistically combine two or more of (a) D-Phenylalanine (DPA) (such as DL-Phenylalanine (DLPA), which is a mixture of DPA and L-Phenylalanine), (b) N-acetyl-L-cysteine (NAC), and (c) kyotorphin (or arginine and tyrosine, the precursors of kyotorphin). (Collectively, as used herein "kyotorphin compound" refers to (a) kyotorphin and (b) arginine and tyrosine, the precursors of kyotorphin). These synergistic compounds of embodiments of the present invention work together to enhance dopamine release by employing mechanisms tied to GABA regulation and increasing enkephalins (by increasing the release of enkepahlins and by the inhibition of enkephalinase). The resulting compound can induce dopamine homeostatis (and thus induce anti-stress states and diminish stress induced addictive behaviors). In embodiments of the present invention, the compound further includes nano-sized particles that enable the compound to be water- or powder-based even though DPA, NAC, and kyotorphin are not soluble in water.

DPA

Phenylalanine is an α-amino acid with the formula $C_6H_5CH_2CH(NH_2)COOH$. This essential amino acid is classified as neutral, and nonpolar because of the inert and hydrophobic nature of the benzyl side chain. The L-isomer is used to biochemically form proteins, coded for by DNA. The codons for L-phenylalanine are UUU and UUC. Phenylalanine is a precursor for tyrosine, the monoamine neurotransmitters dopamine, norepinephrine (noradrenaline), and epinephrine (adrenaline), and the skin pigment melanin.

The stereoisomer D-phenylalanine (DPA) can be produced by conventional organic synthesis, either as a single enantiomer or as a component of the racemic mixture. It does not participate in protein biosynthesis although it is found in proteins in small amounts-particularly aged proteins and food proteins that have been processed. The biological functions of D-amino acids remain unclear, although D-phenylalanine has pharmacological activity at niacin receptor 2.

DL-Phenylalanine (DLPA) is marketed as a nutritional supplement for its supposed analgesic and antidepressant activities. DL-Phenylalanine is a mixture of D-phenylalanine and L-phenylalanine. The reputed analgesic activity of DL-phenylalanine may be explained by the possible blockage by D-phenylalanine of enkephalin degradation by the enzyme carboxypeptidase A. The mechanism of DL-phenylalanine's supposed antidepressant activity may be accounted for by the precursor role of L-phenylalanine in the synthesis of the neurotransmitters and dopamine. Elevated brain levels of dopamine are thought to have an antidepressant effect. D-Phenylalanine is absorbed from the small intestine and transported to the liver via the portal circulation. A small amount of D-phenylalanine appears to be converted to L-phenylalanine. D-Phenylalanine is distributed to the various tissues of the body via the systemic circulation. It appears to cross the blood-brain barrier less efficiently than L-phenylalanine, and so a small amount of an ingested dose of D-phenylalanine is excreted in the urine without penetrating the central nervous system.

"Enkephalinase," a peptidase capable of degradating enkephalins, has been recently characterized in man, in both plasma and cerebro-spinal fluid (CSF). An "enkephalinase inhibitor" (such as DPA) is a type of enzyme inhibitor that inhibits one or more members of the enkephalinase class of enzymes that break down the endogenous enkephalin opioid peptides.

Figure 2:
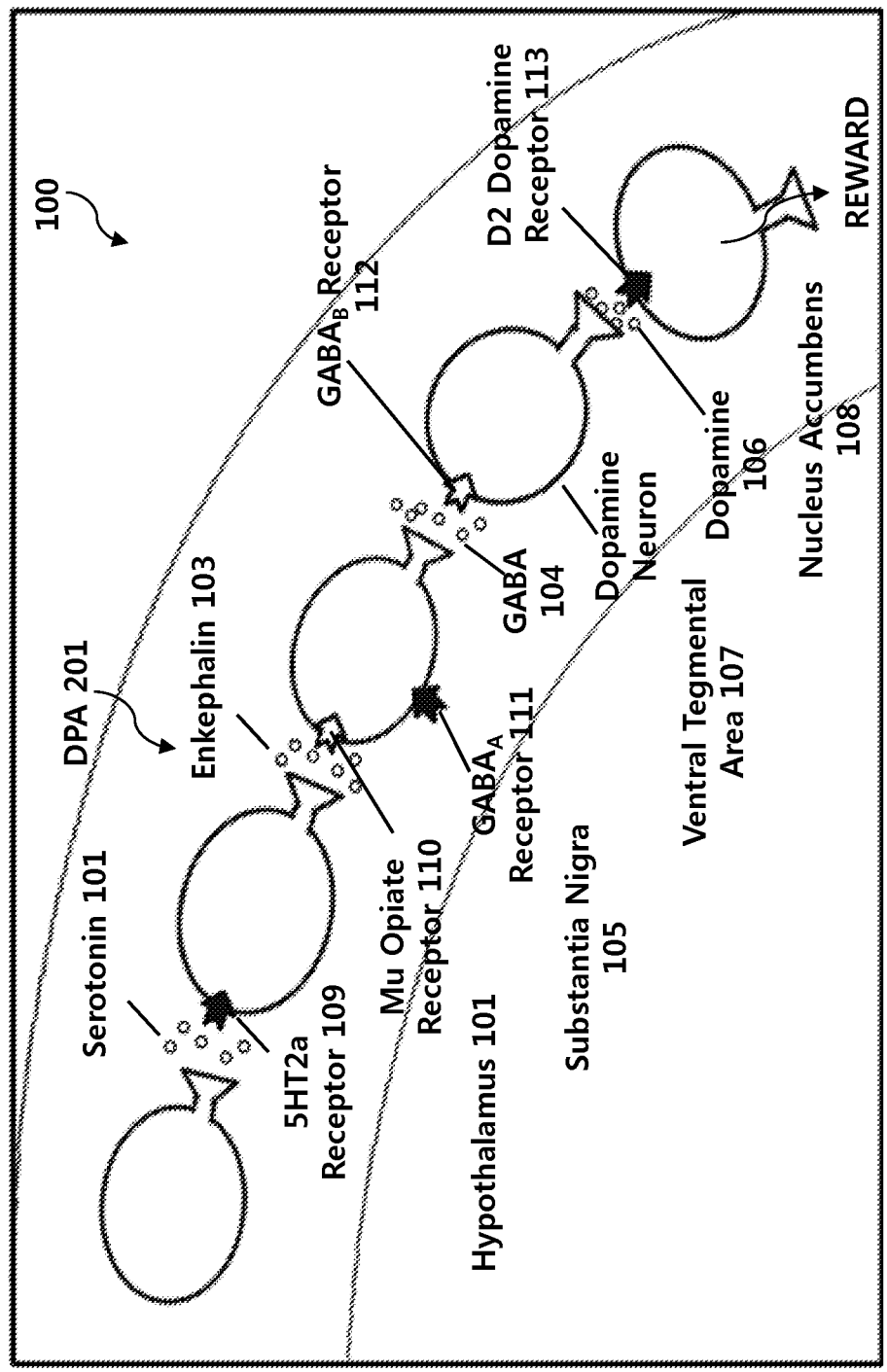
FIG. 2 illustrates the brain reward cascade in which DPA has been introduced in the system.

Referring to FIG. 2, DPA 201 can act to inhibit enkephalinase in the reward cascade 100. Since enkephalinase degrades enkephalins 103, the inhibition of enkephalinase has a net effect of increasing the enkaphalins 103 in the reward cascade. Tracking this through the reward cascade 100, this increase in enkaphalins 103, which means there is more enkaphalins 103 to inhibit GABA 104 at the substantia nigra 105. More inhibition of GABA 104 means there is less GABA 104 in the reward cascade 100. Since GABA 104 regulates the amount of dopamine 106 released at the nucleus accumbens 108 (the reward site), this means that more dopamine 106 is released in response to the DPA 201.

Kyotorphin

Kyotorphin, such as D-kyotorphin (D[arginine-tyrosine]) is a neuroactive dipeptide which plays a role in pain regulation in the brain. Kyotorphin has an analgesic effect, but it does not interact with the opioid receptors. Instead, kyotorphin acts by releasing met-enkephalin and stabilizing it from degradation. It may also possess properties of neuromediator/neuromodulator. Accordingly, kyotorphin is an enkephalin releaser.

Figure 3:
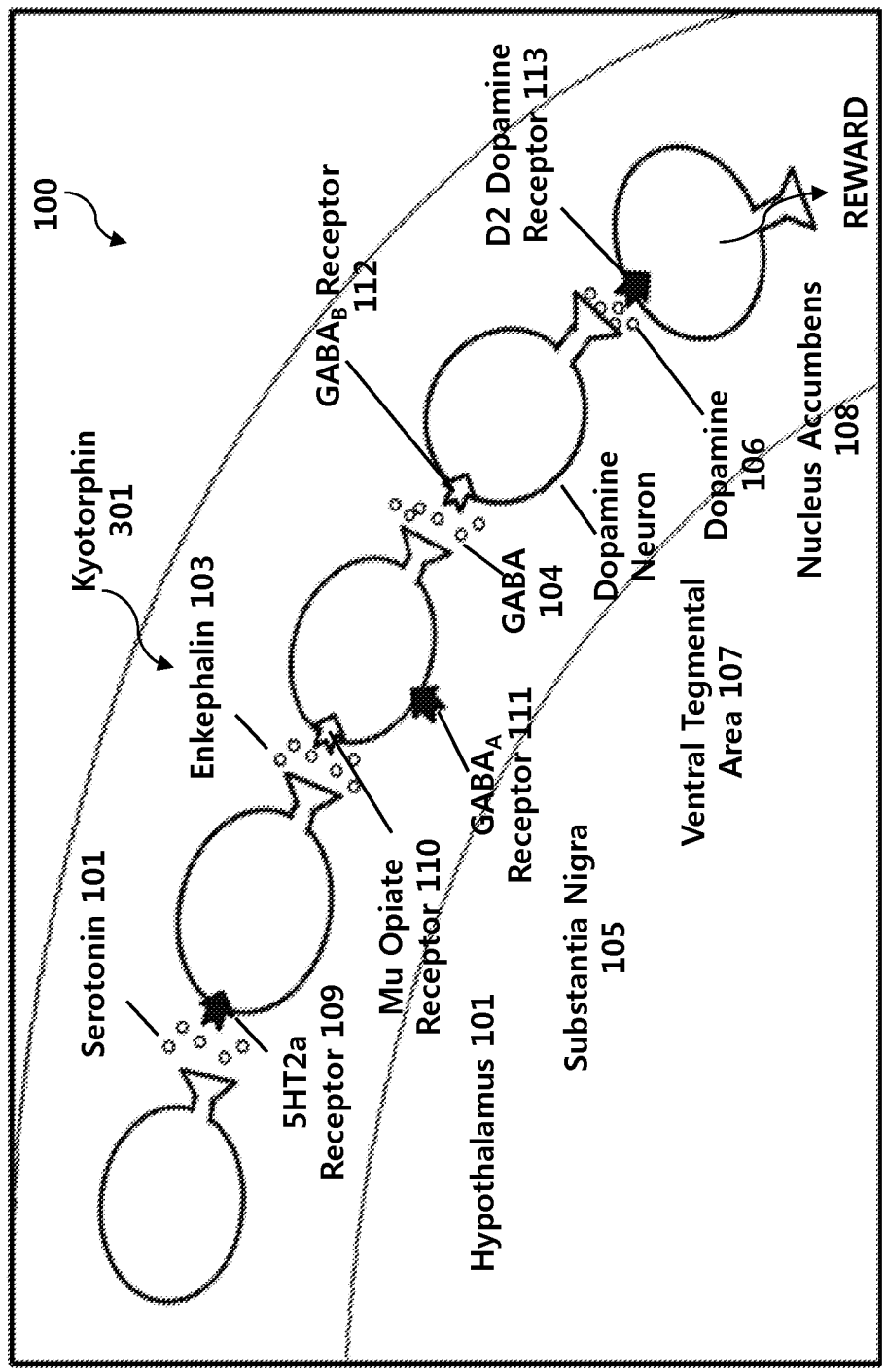
FIG. 3 illustrates the brain reward cascade in which kyotorphin has been introduced in the system.

Referring to FIG. 3, kyotorphin 301 can act to release enkephalins in the reward cascade 100, which increases the enkaphalins 103 in the reward cascade. Tracking this through the reward cascade 100, this increase in enkaphalins 103, means there is more enkaphalins 103 to inhibit GABA 104 at the substantia nigra 105. More inhibition of GABA 104 means there is less GABA 104 in the reward cascade 100. Since GABA 104 regulates the amount of dopamine 106 released at the nucleus accumbens 108 (the reward site), this means that more dopamine 106 is released in response to the kyotorphin 301.

Thus, both DPA and kyotorphin independently result in more dopamine in the reward cascade albeit by different mechanisms. While the DPA inhibits the enkephalinase to indirect raise the enkephalins (which are degraded by enkephalinase), the kyotorphin directly raise the enkephalins (since kyotorphin is a releaser). Hence, DPA and kyotorphin synergistically work together to better control the increase in the amount of enkephalin in the reward cascade.

In some embodiments, the kyotorphin utilized is D-kyotorphin, as it is the most stable form of kyotorphin. The precursors of kyotorphin are arginine and tyrosine. Both arginine and tyrosine are pro-substances for the synthesis of brain kyotorphin. In some embodiments, arginine and tyrosine are used in place of kyotorphin.

NAC

Acetylcysteine, also known as N-acetylcysteine or N-acetyl-L-cysteine (NAC), is a medication used to treat paracetamol (acetaminophen) overdose and to loosen thick mucus such as in cystic fibrosis or chronic obstructive pulmonary disease. It is available by intravenous, by mouth, or inhaled as a mist.

Figure 4:
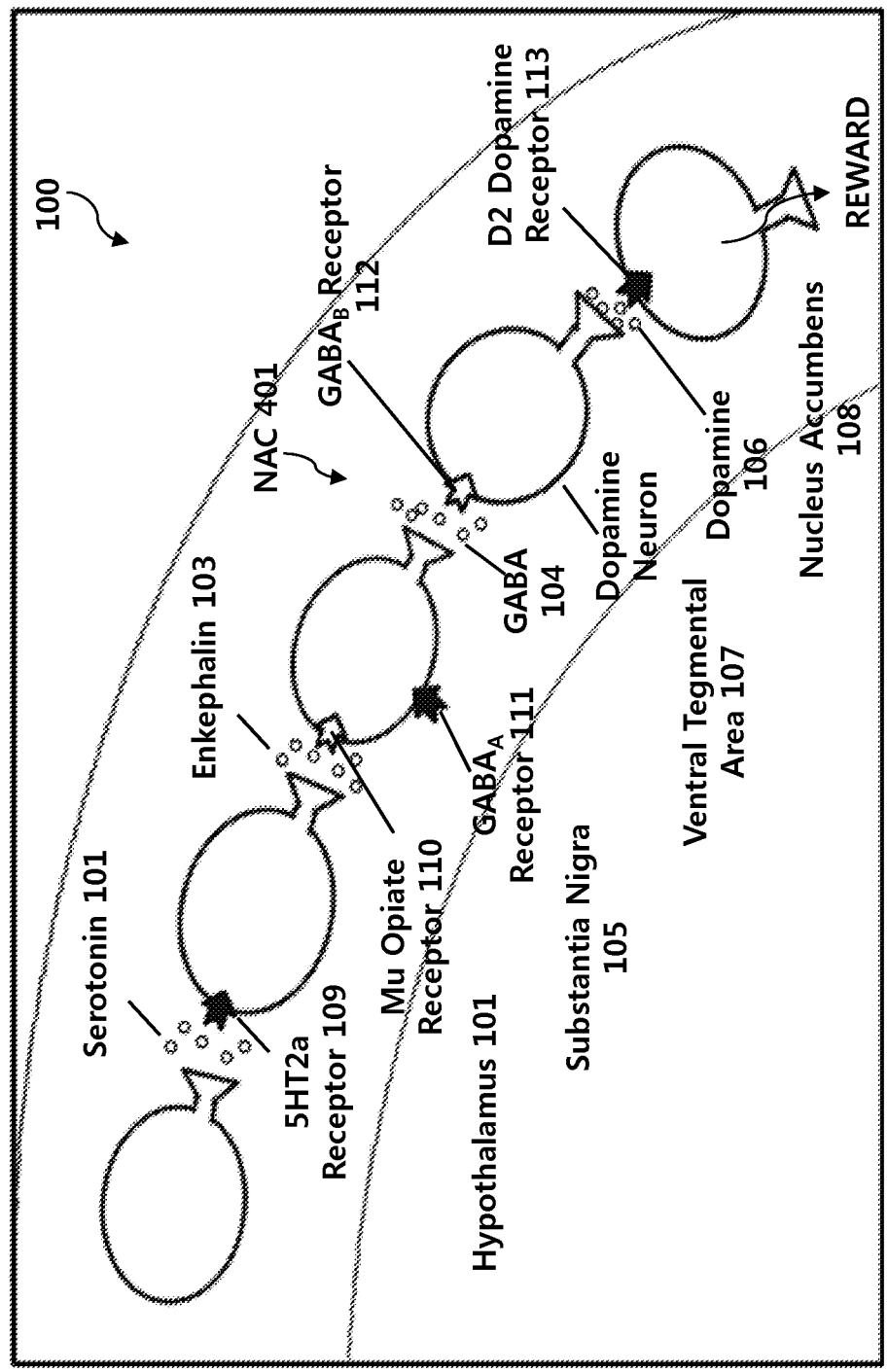
FIG. 4 illustrates the brain reward cascade in which NAC has been introduced in the system.

Referring to FIG. 4, NAC 401 can act to stimulate GABA 104 in the reward cascade 100, which means there is more GABA 104 in the reward cascade 100. Since GABA 104 regulates the amount of dopamine 106 released at the nucleus accumbens 108 (the reward site), this means that less dopamine 106 is released in response to the NAC 401. Hence, the NAC 401 regulates the dopamine 106 in reward cascade 100.

Figure 5:
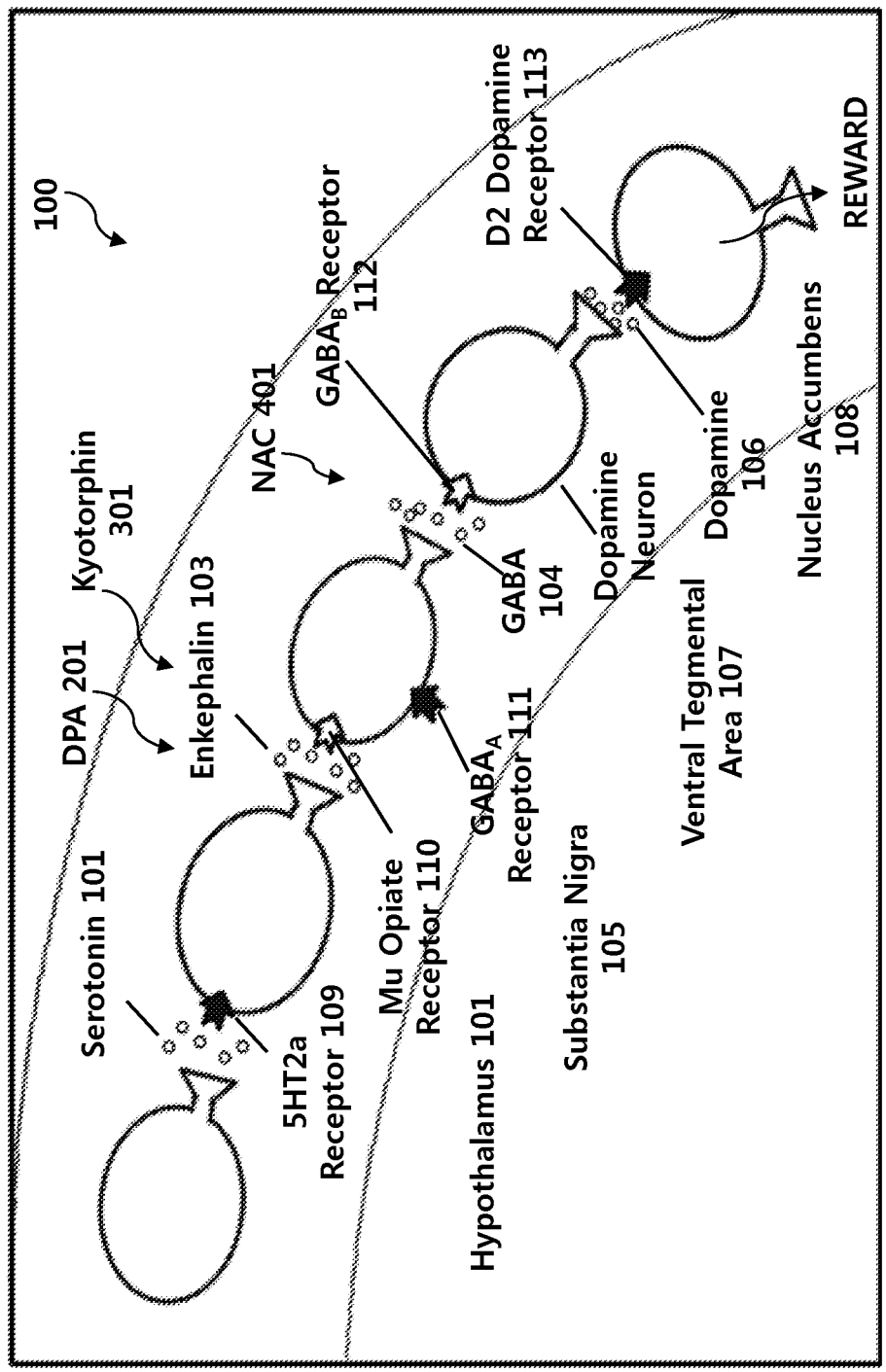
FIG. 5 illustrates the brain reward cascade in which DPA, kyotorphin, and NAC have been synergistically introduced in the system.

When used in used in conjunction with one or both of DPA and kyotorphin (or kyotorphin precursors), this leads to dopamine homeostatis, as the NAC 401 synergistically regulates the dopamine 106 in reward cascade 100. FIG. 5 illustrates the combined use of DPA 201, kyotorphin 301, and NAC 401.

Compositions

Synergistically combining two or more of (a) D-Phenylalanine (DPA) (such as DL-Phenylalanine (DLPA), which is a mixture of DPA and L-Phenylalanine), (b) N-acetyl-L-cysteine (NAC), and (c) kyotorphin (or one or more of arginine and tyrosine, the precursors of kyotorphin) will yield a compound from which dopamine homeostatis is achieved.

For a standard dose, the following ranges have been found to be effective when combining two or more of these:

DPA: 1 to 5000 mg (with a preferred dose of 1,000 mg). The DPA can be in the form of DLPA.

NAC: 1 to 10,000 mg (with a preferred dose of 2,400 mg).

Kyotorphin: For kyotorphin, 0.1 to 5,000 mg (with a preferred dose of 500 mg). The kyotorphin can be D-kyotorphin. For arginine, 0.1 to 1,000 grams (with a preferred dose of 250 mg). The arginine can be L-arginine. For tyrosine, 0.1 to 5,000 grams (with a preferred dose of 150 mg). The tyrosine can be L-tyrosine.

DPA, NAC, arginine, and tyrosine can be obtained from Parchem Fine & Specialty Chemicals (New Rochelle, N.Y.). Kyotorphin can be obtained from ABCAM Biochemicals (Bristol, Mass.).

Embodiments of DLA, NAC, and kyotorphin within these ranges (such as at dosages of 1,000 mg, 2,400 mg, and 500 mg, respectively) can be made in pill or capsule form. However, due to the size, there is difficulty in coating these pills/capsules and also in the taking of these pills/capsules. Moreover, as these were not in liquid form, there are problems with persons (such as addicts) to take these pills/capsules and have these nutrients properly absorbed so that they can synergistically act in the reward cascade. However nano techniques have been developed to even overcome the problems with the pill formulation.

Nanoparticles

DPA, NAC, and kyotorphin (including its precursors) are non-water soluble nutrients, i.e., they each will not readily solubilize in water. To overcome this issue, these materials can be placed in aqueous solutions packaged in micelles or liposomes.

Figure 7:
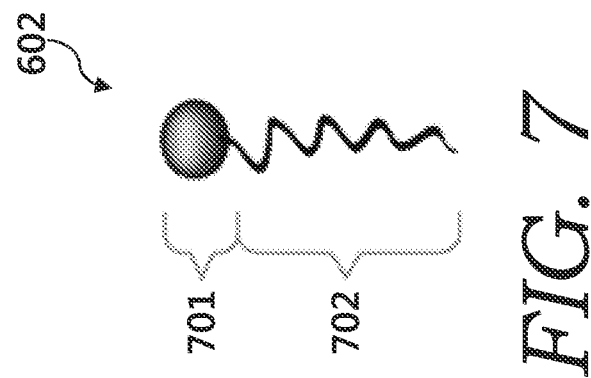
FIG. 7 illustrates a nanoparticle shown in the micelle of FIG. 6.
Figure 6:
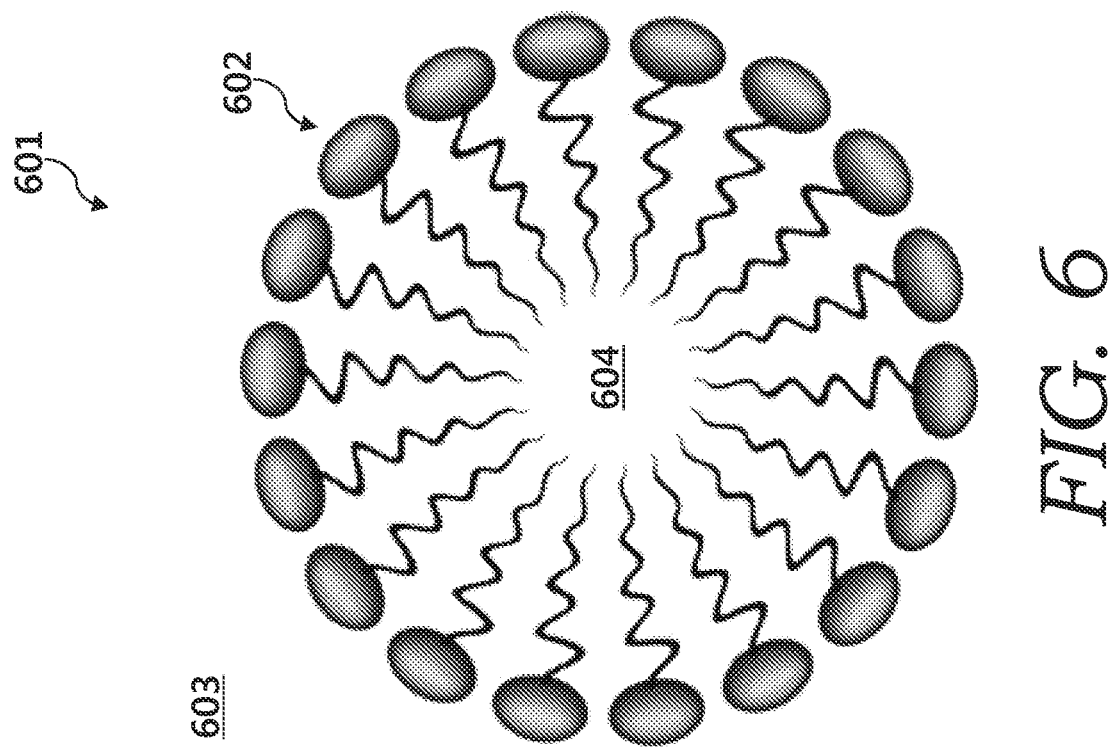
FIG. 6 illustrates a micelle of nanoparticles.

Referring to FIGS. 6-7, a micelle 601 is an aggregate of molecules 602 dispersed in a liquid colloid (typically water) 603. Each molecule 602 has a hydrophilic (i.e., water loving) head region 701 and a hydrophobic (i.e., water hating) tail region 702. A typical micelle 601 in aqueous solution 603 forms an aggregate with the hydrophilic head regions 701 in contact with surrounding solvent 603, sequestering the hydrophobic tail regions 702 in the micelle center 604. This phase is caused by the packing behavior of tail lipids in a bilayer. The difficulty filling all the volume of the interior of a bilayer, while accommodating the area per head group forced on the molecule by the hydration of the head group, leads to the formation of the micelle 601. Generally, micelles are approximately spherical in shape but can be other shapes, such as ellipsoids, cylinders, and bilayers. The shape and size of a micelle are a function of the molecular geometry of the molecules and solution conditions such as concentration, temperature, pH, and ionic strength.

Micelles formation is known as emulsification, a process that allows a compound normally insoluble (in the solvent being used, such as water) to dissolve (in the micelle center 604). Micelle formation is essential for the emulsification and subsequent absorption of fat soluble nutrients like Vitamin E, D, K, the carotenoids and omega-3 EFAs. It is the bile salts formed in the liver and secreted by the gall bladder that allow micelles of fatty acids to form.

Lipid spheres that contain an aqueous core are called liposomes. Liposomes are different from micelles structurally in that they have a bilayer membrane.

In embodiments of the present invention, micelles (or liposomes) are created using nanoparticles in an aqueous solution. A nanoparticle (or nanopowder or nanocluster or nanocrystal) is a small particle with at least one dimension less than 100 nm. These nanoparticles create nanosized vesicles that are water-soluble on the outside and carry the fat soluble nutrient (here two or more of DPA, NAC, and kyotorphin (or one or both of its precursors)) on the inside. Accordingly, the nanoparticles useful in the present invention are those that have a hydrophilic head region, a hydrophobic tail region, are capable of forming micelles or liposomes in an aqueous solution (i.e., water-based solution), and are non-reactive in nature. Preferably, the nanoparticles are also tasteless and are able to be absorbed sublingually.

In certain embodiments, nanoparticles such as those in a liquid product manufactured by AquaPower (American Fork, Utah) can be used. AquaPower's liquid/nano product utilizes principles related to development of small nanoparticles allowing for hydrophobic molecules to act as being hydrophilic, which allows for a delivery system utilized in the present invention.

Such nanoparticles found in the AquaPower water product are generally around 3.17 nm in particle size, non-reactive in nature, tasteless, and are able to be absorbed sublingually with a much higher bioavailability. Generally, the concentration of the nanoparticles used are in the range of 1 ppm to 10 ppm (with 3 ppm for a dose).

Alternatively, the non-liquid ingredients can be formed in to nanoparticles such as by Attostat (North Salt Lake, Utah). Such nanoparticles have a particle size of 10 nm in particle size (in the range of 3 to 20 nm), and are round (nanospheres), non-reactive in nature, tasteless, and allow the composition of the present invention to be absorbed with a much higher bioavailability. Such nanoparticles provide a targeted or directed organ absorption along with a (K) factor filtration. Applicant understands the particle size is reduced by a laser technology to a value of 10 nm without a bell-curved range of ±100 nm as with other types of nano particle size reduction technology. The pH of the nanospheres can be altered in order to obtain greater bio absorption within the gut.

A single dose is generally around 50 mg.

The amount of water in a dose is in the range of 10 ml to 100 ml (generally around 30 ml per dose.

EXAMPLES

Compositions

The following TABLE 2 reflects different compositions made to form a 30 dose supply of 50 mg doses for embodiments of the present invention for mixtures of AquaPower liquid, with two or more of (a) DLPA, (b) NAC, and (c) D-kyotorphin (or L-arginine and L-tyrosine).

TABLE 2

| AquaPower liq (ml) | DLPA (g) | NAC (g) | D-Kyo (g) | L-arginine (g) | L-tyrosine (g) |
| --- | --- | --- | --- | --- | --- |
| 900 | 30 | 72 | 15 | — | — |
| 900 | 30 | 72 | — | — | — |
| 900 | — | 72 | 15 | — | — |
| 900 | 30 | — | 15 | — | — |
| 900 | 30 | 72 | 15 | 7.5 | 4.5 |
| 900 | 30 | 72 | — | 7.5 | 4.5 |
| 900 | — | 72 | 15 | 7.5 | 4.5 |
| 900 | 30 | — | 15 | 7.5 | 4.5 |

The following TABLE 3 reflects different compositions made to form 30 pills for embodiments of the present invention for mixtures of D-kyotorphin (or L-arginine and L-tyrosine) with one or both of (a) DLPA and (b) NAC. These are tablets of nanoparticles.

TABLE 3

| DLPA (g) | NAC (g) | D-Kyo (g) | L-arginine (g) | L-tyrosine (g) | Weight per pill (g) |
| --- | --- | --- | --- | --- | --- |
| 30 | 72 | 15 | — | — | 3.9 |
| — | 72 | 15 | — | — | 2.9 |
| 30 | — | 15 | — | — | 1.5 |
| 30 | 72 | — | 7.5 | 4.5 | 3.8 |
| 30 | — | — | 7.5 | 4.5 | 1.4 |
| — | 72 | — | 7.5 | 4.5 | 2.8 |

Optionally, the following additional nutrients can be added to the compositions: pyridoxal-5-phosphate (the active form of vitamin $B_6$), L-glutamine, *Rhodiola rosea* root SE, rosavin, Griffonia seed extract 5-HTP, L chromium GTF plus, passion flower SE isovitexin, glucosamine n-acetyl, arabinogalactan fiberaid AG99, aloe vera FD powder 200×, white birch bark extract, *Boswellia serrata* gum extract, and *Spirulina* algae. These too are reduced down to nanoparticle size.

Dopamine Homeostasis

A composition (Composition KB220A) as discussed above was made that included the following ingredients:

Pyridoxal-5-Phosphate
Tyrosine, L USP
l-glutamine
*Rhodiola Rosea* Ext (3% Rosavin, 1% Salidroside)
Griffonia Seed SE 99% 5-Hydroxytryptophan
DL Phenylalanine
Kosher GTF Chromium Yeast
Passion Flower Extract 3.5-4% Vitexins
N Acetyl Cysteine
N Acetyl D-Glucosamine
Larch Arabinogalactans
Organic Aloe Vera Gel Powder 200:1 #700
White Birch Bark 4:1 Extract
*Spirulina*

These materials were dispersed into AquaPower liquid to form Composition KB220A. The nanoparticles in the AquaPower liquid formed micelles within the water and the NAC, DLPA, and the other ingredients were dissolved therein.

Sixteen moderate to heavy opioid addicts were detoxified at the Pure Recovery Treatment Center in Los Angeles Calif. using Composition KB220A. Out of the sixteen individuals only two people have relapsed.

The first 6 patients received at least 2 ounces twice a day of KB220A along with clonipine and some benzodiazepines. Following the six day detoxification period, all six people were continued on Composition KB220A daily at 1 to 2 ounces per day. Following treatment of 20-45 days, the six patients all received Composition KB220A as a take home anti-RDS compound. Follow-ups with these patients after 90 days have revealed that 5 of the 6 patients are still sober. One individual did report a relapse.

Moreover, in an additional four patients, the dose of Composition KB220A was increased to 4 ounces every 4 hours and, as before, also included clonipine and some benzodiazepines. The detox withdrawal was significantly lower in the second population with the higher dose. In these four patients, one did relapse and the other three have been stabilized with Composition KB220A for over 60 days.

Finally, six additional patients were detoxified from opioids using the higher dose of Composition KB220A for a six day period with very positive results.

An important feature about this clinical trial was that only two of the sixteen patients studied required buprenorphine/naloxone for stabilization during the six day period. This was very encouraging because most opioid addicts are administered a buprenorphine/naloxone combination to prevent withdrawal symptoms. Accordingly and remarkably, the compositions of the present invention can be used by opioid addicts for detoxification without the usual buprenorphine/naloxone.

For the group tested, this means that, without the need for buprenorphine/naloxone, Composition Kb220A induced lower rates of withdrawal symptoms in 14/16 patients or 88%. The total rate of relapse was 2/16 (range 6-90 days) or 12%, which is very low since relapse rates are as high as 90%.

While embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, other embodiments are within the scope of the following claims. The scope of protection is not limited by the description set out above, but is only limited by the claims which follow, that scope including all equivalents of the subject matter of the claims.

The disclosures of all patents, patent applications, and publications cited herein are hereby incorporated herein by reference in their entirety, to the extent that they provide exemplary, procedural, or other details supplementary to those set forth herein.

REFERENCES

U.S. Pat. No. 6,132,724, entitled "Allelic Polygene Diagnosis Of Reward Deficiency Syndrome And Treatment," issued Oct. 17, 2000, to Blum ("Blum '724 Patent").

U.S. Pat. No. 6,955,873, entitled "Diagnostic and Treatment System For Reward Deficiency Syndrome (RDS) And Related Behaviors," issued Oct. 18, 2005, to Blum ("Blum '873 Patent").

C. M. Adler, "Effects of acute metabolic stress on striatal dopamine release in healthy volunteers," *Neuropsychopharmacolgy*, 2000, 22(5):545-50 ("Adler 2000").

K. Blum et al., "Buprenorphine Response as a Function of Neurogenetic Polymorphic Antecedents: Can Dopamine Genes Affect Clinical Outcomes in Reward Deficiency Syndrome (RDS)" *J Addict Res Ther.*, 2014, 5 pii: 1000 ("Blum 2014").

K. Blum et al., *Molecular Neurobiology of Addition Recovery: The 12 Steps Program and Fellowship*, Springer Science & Business Media (2013) ("Blum 2013").

K. Blum et al., "Generational association studies of dopaminergic genes in reward deficiency syndrome (RDS) subjects: selecting appropriate phenotypes for reward dependence behaviors," *Int J. Environ Public Health*, 2011, 8(12):4425-59.

K. Blum et al., "Reward deficiency syndrome: a biological model for diagnostics and treatment of impulsive, additive, and compulsive behavior," *J. Psychoactive Drugs*, 2000, 32 Suppl: 1-iv, 1-112 ("Blum 2000").

K. Blum et al., "The D2 dopamine receptor gene as a determinant of reward deficiency syndrome," *J R Soc. Med*, 1996, 89(7):396-400 ("Blum 1996").

K. Blum K. et al., "Allelic association of human dopamine D2 receptor gene in alcoholism," *JAMA*, 1990, 263(15), 2055-2060 ("Blum 11990").

K. Blum K. et al., "Ethanol and neuromodulator influences. A cascade model of reward," *Alcohol and behavior: Basic and clinical aspects*, (ed. H Ollat et al.), 1990 ("Blum II 1990").

A. Bowirrat et al., "Relationship Between Dopaminergic Neurotransmission, Alcoholism, and Reward Deficiency Syndrome," *American Journal of Medical Genetics Part B (Neuropsychiatric Genetics)*, 2005 132B:29-37 ("Bowirrat 2005").

G. Di Chiara et al., "Drugs abused by humans preferentially increase synaptic dopamine concentrations in the mesolimbic system of freely moving rats," *Proc Natl Acad Sci USA*, 1988, 85:5274-5278 ("Di Chiara 1988").

D. E. Comings et al., "Reward deficiency syndrome: genetic aspects of behavioral disorders," *Prog Brain Res*, 2000, 126:325-41 ("Comings 2000").

C. Dackis et al., "Neurotransmitter and neuroendocrine abnormalities associated with cocaine use," *Psychiatr Med.*, 1985, 3(4):461-483 ("Dackis 1985").

D. T. Eisenberg et al., "Season of birth and dopamine receptor gene associations with impulsivity, sensation seeking and reproductive behaviors," *PLoS One*, 2007, 2:e1216 ("Eisenberg 2007").

G. I. Gessa et al., "Low doses of ethanol activate dopaminergic neurons in the ventral tegmental area," *Brain Research*, 1985, 348: 201-203 ("Gessa 1985").

R. D. Hall et al., "Neuronal and neurochemical substrates of reinforcement," *Neuroscience Research Program Bulletin*, 1977, 15:131-314 ("Hall 1977").

J. Hietala et al., "Striatal D2 dopamine receptor binding characteristics in vivo in patients with alcohol dependence," *Psychopharmacology (Berl)*, 1994, 116:285-290 ("Hietala I 1994").

J. Hietala J et al., "Striatal D2 dopamine receptor characteristics in neuroleptic-naive schizophrenic patients studied with positron emission tomography," *Arch Gen Psychiatry*, 1994, 51:116-123 ("Hietala II 1994").

A. E. Kelley et al., "The Neuroscience of natural Rewards: Relevance to Addictive Drugs," *J. Neurosci*, 2002, 22(9): 3306-3311 ("Kelley 2002").

M. Melis et al., "The dopamine hypothesis of drug addiction: hypodopaminergic state," *Int Rev Neurobiol*, 2005, 63:101-154 ("Melis 2005").

R. D. Myers et al., "Mu and D2 receptor antisense oligonucleotides injected in nucleus accumbens suppress high alcohol intake in genetic drinking HEP rats," *Alcohol*, 1999, 18(2-3):225-233 ("Myers 1999").

L. H. Parsons et al., "Serotonin Ib receptor stimulation enhances dopamine-mediated reinforcement, *Psychopharmacol*, 1996, 128:150-160 ("Parson 1996").

R. Picetti et al., "Addiction and stress clues for cocaine pharmacotherapies," *Current Pharmaceutical Designs*, 2013, 18(40), 7065-7080 ("Picetti 2013").

J. Qi et al., "A Glutamatergic Reward Input From The Dorsal Raphe To Ventral Tegmental Dopamine Neurons," *Nat Commun.*, 2014, 5:5390 ("Qi 2014").

T. W. Robbins, "Neurobehavioural mechanisms of reward and motivation," *Curr Opin Neurobiol.*, 1996, 6(2):228-236 ("Robbins 1996").

R. B. Rothman et al., "Dual dopamine/serotonin releasers as potential medications for stimulante and alcohol addictions," *AAPS J*, 2007, 9(1): E1-E10 ("Rothman 2007").

P. K. Thanos et al., "Overexpression of dopamine D2 receptors reduces alcohol self-administration," *J. Anal. Toxicol.*, 2001, 25, 410-424 ("Thanos 2001").

N. D. Volkow et al., "Role of dopamine, the frontal cortex and memory circuits in drug addiction: insight from imaging studies," *Neurobiol Lern Mem*, 2002, 78:610-24 ("Volkow 2002").

N. D. Volkow, et al., "Low level of brain dopamine D2 receptors in methamphetamine abusers: association with metabolism in the orbitofrontal cortex," *Am J Psychiatry*, 2001, 158:2015-2021 ("Volkow 2001").

N. D. Volkow, et al., "PET evaluation of the dopamine system of the human brain," *J. Nucl. Med*, 1996, 37, 1242-1256 ("Volkow 1996").

G. Yadid et al., "Endogenous serotonin stimulates striatal dopamine release inconscious rats," *J Pharmacol Exp Ther*, 1994, 270:1158-1165 ("Yadid 1994").

What is claimed is:

1. A composition comprising:
   (a) water;
   (b) a plurality of nanoparticles dispersed within the water, wherein
      (I) the water and the plurality of nanoparticles are in a form of an emulsion comprising a plurality of micelles or liposomes within the water, and
      (II) each micelle or liposome within the plurality of micelles or liposomes comprise an aggregate of some of the plurality of nanoparticles arranged in a micelle or liposome form within the water; and
   (c) at least two substances dispersed within the water, wherein the at least two substances are at least two of (i) DPA, (ii) NAC, and (iii) a kyotorphin compound selected from the group consisting of (A) kyotorphin and (B) a combination of arginine and tyrosine, and wherein
      (I) the at least two substances are dissolved within the micelles or liposomes.

2. The composition of claim 1, wherein the at least two substances comprises the DPA, the NAC, and the kyotorphin compound.

3. The composition of claim 1, wherein the at least two substances comprises the DPA.

4. The composition of claim 3, wherein the DPA is DLPA.

5. The composition of claim 1, wherein the at least two substances comprises the NAC.

6. The composition of claim 1, wherein the at least two substances are present in the composition at a dosage operable to induce dopamine homeostasis.

7. The composition of claim 6, wherein the dosage comprises at least two of
   (i) the DPA in a DPA amount in the range of 1 to 5,000 mg,
   (ii) the NAC in an NAC amount in the range of 1 to 10,000 mg, and
   (iii) the kyotorphin compound selected from the group consisting of (A) kyotorphin in a kyotorphin amount in the range of 0.1 to 5,000 mg and (B) the combination of the arginine and the tyrosine, wherein the arginine is in an arginine amount in the range of 0.1 to 1,000 grams and the tyrosine is in a tyrosine amount in the range of 0.1 to 5,000 grams.

8. The composition of claim 7, wherein
   (i) the DPA is DLPA,
   (ii) the kyotorphin comprises D-kyotorphin,
   (iii) the arginine comprises L-arginine, and
   (iv) the tyrosine comprises L-tyrosine.

9. The composition of claim 8, wherein
   (i) the DPA amount is 1,000 mg,
   (ii) the NAC amount is 2,400 mg,
   (iii) the kyotorphin amount is 500 mg,
   (iv) the arginine amount is 250 mg, and
   (v) the tyrosine amount is 150 mg.

10. The composition of claim 7, wherein
    (i) the DPA is DLPA,
    (ii) the arginine comprises DL-arginine, and
    (iii) the tyrosine comprises DL-tyrosine.

11. The composition of claim 1, wherein the plurality of nanoparticles form micelles within the water and the at least two substances are dissolved within the micelles.

12. The composition of claim 1 further comprising an additional substance dispersed in the water, wherein the additional substance is selected from the group consisting of pyridoxal-5-phoshate, L-glutamine, *Rhodiola rosea* root SE, rosavin, Griffonia seed extract 5-HTP, L chromium GTF plus, passion flower SE isovitexin, glucosamine n-acetyl, arabinogalactan fiberaid AG99, aloe vera FD powder 200X, white birch bark extract, *Boswellia serrata* gum extract, and *Spirulina* algae.

* * * * *